United States Patent
Walz et al.

[11] Patent Number: 6,149,656
[45] Date of Patent: Nov. 21, 2000

[54] ELECTRODYNAMIC LITHOTRIPTOR

[75] Inventors: Volker Walz, Rohrdorf; Konrad Schaefer, Hamburg, both of Germany

[73] Assignee: Volker Walz, Rohrdorf, Germany

[21] Appl. No.: 09/388,872

[22] Filed: Sep. 2, 1999

[30] Foreign Application Priority Data

Sep. 11, 1998 [DE] Germany .......................... 198 41 628
May 11, 1999 [DE] Germany ........................ 299 09 422 U

[51] Int. Cl.[7] .................................................. A61B 17/22
[52] U.S. Cl. .......................................... 606/128; 606/127
[58] Field of Search .................................. 606/127, 128, 606/107, 19, 22, 170, 902, 171, 184, 185

[56] References Cited

U.S. PATENT DOCUMENTS

| 4,227,532 | 10/1980 | Bluhm et al. ............................ 606/127 |
| 5,011,821 | 4/1991 | McCullough ................................ 505/1 |
| 5,540,702 | 7/1996 | Walz ........................................ 606/128 |
| 5,741,272 | 4/1998 | Kuhne ....................................... 606/128 |
| 5,868,756 | 2/1999 | Henry et al. ............................. 606/128 |
| 5,906,623 | 5/1999 | Peterson .................................. 606/128 |

FOREIGN PATENT DOCUMENTS 3923215  4/1991  Germany ................ 606/128

*Primary Examiner*—Pedro Philogene
*Attorney, Agent, or Firm*—Pearne & Gordon LLP

[57] ABSTRACT

An apparatus to introduce impact pulses into the human body has an impact transmitter (8) displaceable in an axial direction and an electromagnetic impact generator (2, 6; 26, 24; 36, 34) driven by current pulses and supplying force impulses to the impact transmitter. The impact generator includes a magnet fixed in position and having a magnetic field, and a coil (6, 26, 36) displaceable in the direction of transmitter displacement in the field of the magnet (2; 23, 24; 33, 34), the coil being energized by the current pulses to be axially displaced and drive the impact transmitter (8).

9 Claims, 3 Drawing Sheets

ELECTRODYNAMIC LITHOTRIPTOR

FIELD OF THE INVENTION

The present invention relates to apparatus for transmitting impact impulses into a selected region in the body of a patient, the apparatus having particular use in urological lithotripsy.

BACKGROUND OF THE INVENTION

Concretions in patients' bodies, for instance gall stones and in particular kidney stones, are only rarely removed surgically at present, but are predominantly destroyed in situ, after which the destroyed residues can be naturally evacuated. Various methods of destruction are known in this respect. The classical method, presently widely abandoned, consists of using mechanical crushing tongs. By means of highly complex large apparatus, the stone can be destroyed by using concentrated hydraulic waves ultrasonically generated outside the body and passing through the body. In another procedure, electro-hydraulic shock waves are generated in the immediate vicinity of the stone. Stones furthermore are destroyed using laser pulses or by contact with ultrasonic vibrators.

In recent years, mechanical destruction has been successful employing an impact wire to which are applied impact pulses. This impact wire is supplied with impact impulses at its proximal end by an impact generator, the impact impulse being a mechanical pulse having a very steep rise flank and causing compression of the proximal end of the impact wire, this compression propagating as an impact pulse through the wire and driving the distal end of the impact wire into axial extension, whereby the body's concretion within the excursion zone is easily destroyed. The required wire has a diameter, for instance, of 1–2 mm and a length, for instance, of 50 cm and is very easily inserted into the body, such as through the urethra of the patient as far as a urethral stone which is typically situated in the upper end region of the urethra.

In known apparatus of this kind, the impact pulse is generated at the proximal end of the impact wire by being hit by a mass shaped like a projectile and reciprocatingly driven in the longitudinal direction of the impact wire. According to European patent document B1 0,317,507, this projectile may be driven pneumatically.

Apparatus of this general type is known from German patent document A1 4,313,768. In this disclosure, the impact generator is electromagnetic. A stationary coil energized with current pulses accelerates a heavy mass designed as a magnetic core in the axial direction of the impact wire over a fairly substantial path until it impacts this wire with high momentum.

The last two above designs substantially offer the same advantages and incur the same drawbacks. They manage to generate impact pulses in impact wires, for instance 1–2 mm in diameter and made of spring steel, by being impacted by the mass, said pulses driving the distal end face of the impact wire into excursions of about 1 mm at speeds up to about 20 m/s in a manner suitable to destroy body concretions. However, this design suffers from the drawback of the impact principle, which entails high stress on the impact surface and commensurate maintenance. Moreover, the duration and intensity of impact is inherently not adjustable in the known apparatus. Only the impact speed of the mass and hence the intensity of impact can be controlled. Therefore, the shock pulses can be matched to requirements only in a very limited way. Again, this design entails a comparatively large and heavy impact generator which must be hand-held. This generator when in operation is fairly noisy and generates strong vibrations which are irksome during treatment.

SUMMARY OF THE INVENTION

An object of the present invention is to improve apparatus of the above described type as to simplicity of maintenance and handling features.

In conventional lithotriptor devices, the proximal end must be supplied with a hard, short, high-energy impact. The state of the art's implementation resorts to hitting a mass accelerated over a substantial path. Opinion has heretofore held that this was the only way to attain an adequately large impact pulse. In the invention, on the other hand, a current pulse is applied to the impact wire by a coil displaced within a magnetic field. A spool within the coil may be very lightweight and can be accelerated at high force over a short path. Therefore the spool can generate the impact pulse in the impact wire by its movement even when being in direct contact with the wire. Moreover, after moving through a short path, the spool can impact the impact wire in order to gain a larger acceleration excursion. In every case, however, there is the advantage that the firmly coupled spool, or the spool moving to impact after a slight path, can be very lightweight and that consequently the impact sites suffer no significant wear. As a result, the substantial wear-entailed problems of the known designs are wholly avoided. Illustratively, the impact wire no longer needs to be exchanged on account of wear. Since the impact wire no longer needs to be exchanged, the design of the apparatus of the invention also can be simplified with respect to maintenance, namely disassembly, and it can be improved further as regards the complete encapsulation demanded by sterility. The required electrical pulse energy being substantially the same as in the known apparatus, the electrical pulse generator used in the latter is also plainly applicable in the apparatus of the invention, remaining substantially unmodified. As regards the apparatus of the invention, and as is known from loudspeaker drive systems, the very light coil can be appropriately controlled, for instance by shaping, and by selecting the height and width of the current pulse, it is easily possible to electrically match the impact amplitude, impact duration and impact intensify of the impact pulse generated in the impact wire to the requirements, quite easily, without need for mechanical adjustment of the mechanical structure. As in loudspeaker drive systems, the coil may be supplied either directly through electrical leads with the current pulses and be mounted in an illustratively DC magnetic field, or else, for instance, it may also be supplied indirectly, in the form of a transformer's shorted turn, with current pulses while generating a repulsion force relative to the field of the current-carrying electromagnet. In the latter case as well, there results a design again simplified and without the need to generate a permanent magnetic field. The apparatus of the invention is of substantially smaller and lighter design and hence more easily handled, and also it is quieter and can be operated more reliably. The apparatus of the invention is applicable in particular to lithotripsy in the human body, the transmitter being, for example, in the form of the conventional impact wire. However, the apparatus of the invention also is applicable in other medical fields where it is desired, for instance, to introduce impact pulses into the human body illustratively from the skin surface. In that case the transmitter may be formed as a plate or pane resting on the surface of the body to introduce the impact across contacting surfaces.

It is advantageous to use the electrodynamic principle used in loudspeakers, namely a current-carrying coil in a magnetic field. The magnet may be an electromagnet or preferably a conventional permanent magnet.

The coil per se may rest directly in contact against the proximal end of the transmitter. Preferably however a coupling structure is provided to transfer the impact between coil and transmitter. This transmitter may be in the form of a funnel structure, hereafter called funnel, for advantageous impedance matching of the larger coil diameter at one side to the smaller diameter of an impact wire at the other side.

The coupling preferably is a transverse plate allowing surprisingly advantageous linkage. This plate may be used per se as the transmitter in apparatus used for surface impact introduction through a tissue surface.

In the above embodiment, the coil is directly loaded through appropriate leads, in the manner of loudspeaker technology, with current pulses. This coil is configured in the static magnetic field of a permanent magnet or in that generated by a DC-energized electromagnet. In an advantageous alternative, the coil may be a short-circuit turn configured in the field of an electromagnet loaded with current pulses and consequently generating magnetic field pulses. In this process, the abruptly generated magnetic field of the electromagnet induces a current in the shorted turn to drive the coil in a manner similar to the above embodiment. The impacts so attained are of approximately the same magnitude as in the previous design. The advantage, however, is the substantially simpler design of the moving coil which illustratively may be a simple ring or a bush made of an appropriately electrically conducting material such as copper. Aluminum is preferred on account of good conductivity and low weight.

In this respect, the winding producing the electromagnet's magnetic field is affixed to this magnet around a magnetizable core passing through both the winding and the short-circuiting coil. The winding acts as a transformer- primary generating an opposing current in the shorted coil acting as the secondary. When a current pulse is applied to the winding, the shorting coil is repelled with great force over the core away from the winding. This represents a significant simplification whereby especially external magnetic fields are generated only during pulse application. Permanent magnetic phenomena in the ambience such as are created by permanent magnets are then avoided.

In another embodiment, a field ring is able to appropriately concentrate the magnetic field in the vicinity of the coil, which in this instance is an aluminum ring, to raise the efficiency of the apparatus.

Apparatus using an impact wire insertable into the body to the location of a concretion is useful in particular in conventional urological lithotripsy.

BRIEF DESCRIPTION OF THE DRAWINGS

The invention is diagrammatically and illustratively shown in the accompanying drawings wherein.

DETAILED DESCRIPTION OF PREFERRED EMBODIMENTS

Figure 1:
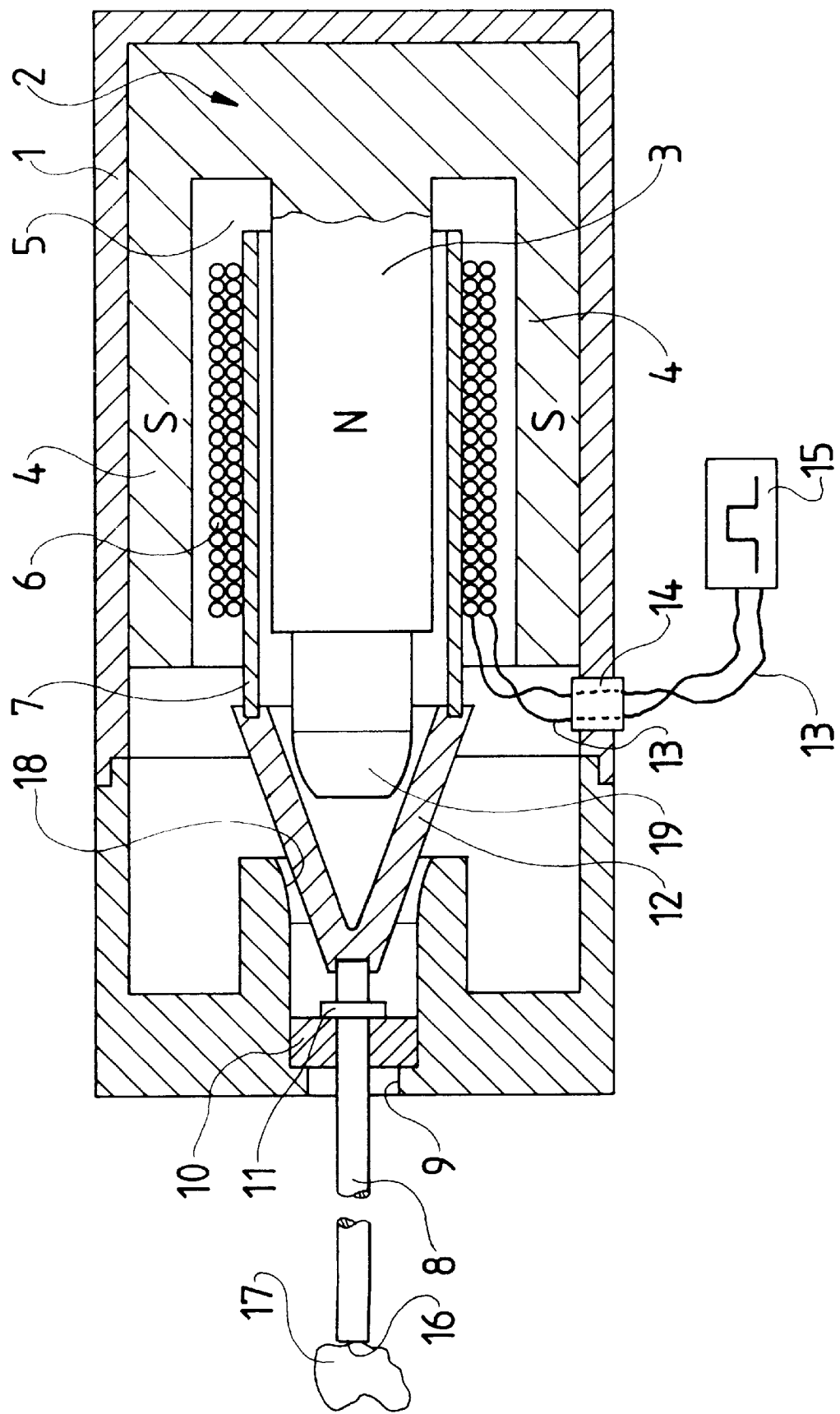
FIG. 1 is an axial section of a first embodiment of the invention of apparatus fitted with a drive system.

FIG. 1 shows a first embodiment of the invention wherein a permanent magnet 2, which also may be replaced by a DC energized electromagnet, is received within a two-part housing 1. Permanent magnet 2 comprises an inner pole piece 3 and an external pole piece 4 enclosing the inner pole piece 3 concentrically and in a capping manner. A cylindrical gap 5 is formed between inner pole piece 3 and external pole piece 4. Illustratively, inner pole piece 3 and external pole piece 4 are the north and south poles of a permanent magnet, as shown in the Figure, as a result of which a strong magnetic field up to 1 Tesla, for instance, can be formed in cylindrical gap 5 radially to the axis of inner pole piece 3.

A coil 6, which in this embodiment comprises two layers of wire, is mounted in cylindrical gap 5 and is conventionally affixed to a support 7 in the form of a rigid, thin tube, for instance, by being bonded to the tube.

A conventional impact wire 8, illustratively having a 1–2 mm diameter and a length, for instance, of 50 cm, is used to destroy kidney stones and is made of spring steel. While being coaxial with inner pole piece 3, the proximal end of impact wire 8 projects through an aperture 9 in housing 1, into the housing inside. An elastic block 10 penetrated by impact wire 8 is mounted in aperture 9 in which it is held against outward movement by the shown offset. A collar 11 affixed to impact wire 8 rests internally against block 10. On one hand, block 10 seals the housing with respect to impact wire 8 and on the other hand it elastically returns the impact wire after each impact.

At its proximal end, impact wire 8 makes contact with the tip of a funnel 12 which acts as the coupling between the impact wire and the coil. In the embodiment shown, the impact wire is slightly inset in the funnel tip for purposes of centering.

Funnel 12 flares toward the coil 6 and its edge is affixed to the end of support 7 projecting from cylindrical gap 5. In this embodiment, for purposes of centering, the front end of support 7 is inserted into a groove in the funnel edge.

Funnel 12 transmits impact from support 7 to impact wire 8. For that purpose, these parts must be kept in play-free contact allowing excellent impact transmission. Accordingly, these parts may be screwed to each other, clamped together or be affixed in a contacting manner in some other way. However, they also may merely rest against one another without any affixation. In this latter case, however, coil 6 must be permanently mechanically biased by appropriate means into contact with impact wire 8. Illustratively, a spring, not shown, may be inserted between the proximal end of the coil and the end of cylindrical gap 5. Such permanent contact by the coil also can be implemented, for instance, electrically using a DC bias. In such a contacting manner, elastic block 10 also may be used to elastically press the impact wire against coil 6.

Coil 6 is connected by electrical leads 13 through a feed-through 14 in housing 1 to an electric pulse generator 15 which applies electric current pulses to coil 6 to generate mechanical impact forces.

In one embodiment, permanent magnet 2 and coil 6 may be in the form of a conventional loudspeaker drive system. In this case, the electrical coil impedance is about 8 ohm at approximately 100 turns. Pulse generator 15 generates voltage pulses of about 2,000 v at a width of about 50 $\mu s$. For repeated impacts, current pulses also can be repeated short-term or be generated in series. Impact parameters such as width, amplitude and pulse shape and the like can be electrically predetermined in a desired manner.

When an electrical pulse of appropriate polarity runs through coil 6, this coil is impulsively accelerated toward impact wire 8. The impact pulse is transmitted by support 7 to the edge of funnel 12 and from the funnel's tip to the impact wire. The acceleration by coil 6 and rigid funnel 12 is so high at the proximal end of the impact wire 8 that this wire is compressed at its proximal end zone. As a result, an impact pulse is introduced into the impact wire and run through this wire to its distal end surface 16 where it causes an excursion of this end surface. A contacting body concretion, for instance the shown kidney stone 17, is then destroyed by this applied impact.

The shape and material of funnel 12 are significant parameters regarding impedance matching between coil 6, or its support 7, and impact wire 8 in order to reduce impact reflections or decelerations. The hollow design of funnel 12 of the conical coupling element is advantageous in this respect. Funnel 12 may be metallic or, illustratively, may also consist of a hard plastic.

In the embodiment shown in FIG. 1, the impact generator is a substantially conventional loudspeaker drive system wherein coil 6 transmits the impact it generates to support 7 which, in turn, applies the impact to funnel 12. To eliminate any resiliency or other adverse impact effects through support 7, a design furthermore may be used wherein the distal end face of coil 6 rests directly against the edge of funnel 12, so that the impact generated by coil 6 is transmitted directly.

To keep coil 6 centered in annular gap 5 and to preclude damaging side movements from contacting permanent magnet 2, a conventional centering loudspeaker spider may be used, illustratively outside the end of external pole piece 4 to connect it, that is the housing 1, in elastically centering manner to support 7.

However, as regards the embodiment of FIG. 1, coil 6 is centered in a different way. An annular surface acting as a centering rest 18 is present at the inside end of aperture 9. A limit body forming an annular centering body 19 is affixed to inner pole piece 3. Funnel 12 is able to move axially, with respect to the apparatus, between centering rest 18 and centering body 19 to allow a slight excursion of a few tenths of a mm which is adequate to load impact wire 8, after which this funnel is centered by contact of its outside surface against centering rest 18 or by its inside surface contacting centering body 19. Accordingly, the funnel is centered at both ends of its displacement. Moreover, this design provides desirable limitation of axial motion, also as regards the motion of impact wire 8, as a result of which this wire cannot be hurled away when exposed to the impact energy.

In the embodiment of FIG. 1, impact wire 8, funnel 12 acting as the coupling element and support 7 carrying coil 6 are firmly joined together without play. However, they may alternatively be separate, for instance, support 7 may be separate from funnel 12, so that coil 6 by means of its support 7 impacts the end face of funnel 12 only after a predetermined short path. In this manner, the effective stroke of coil 6 in the magnetic field and hence the impact energy may be increased somewhat further.

Figure 2:
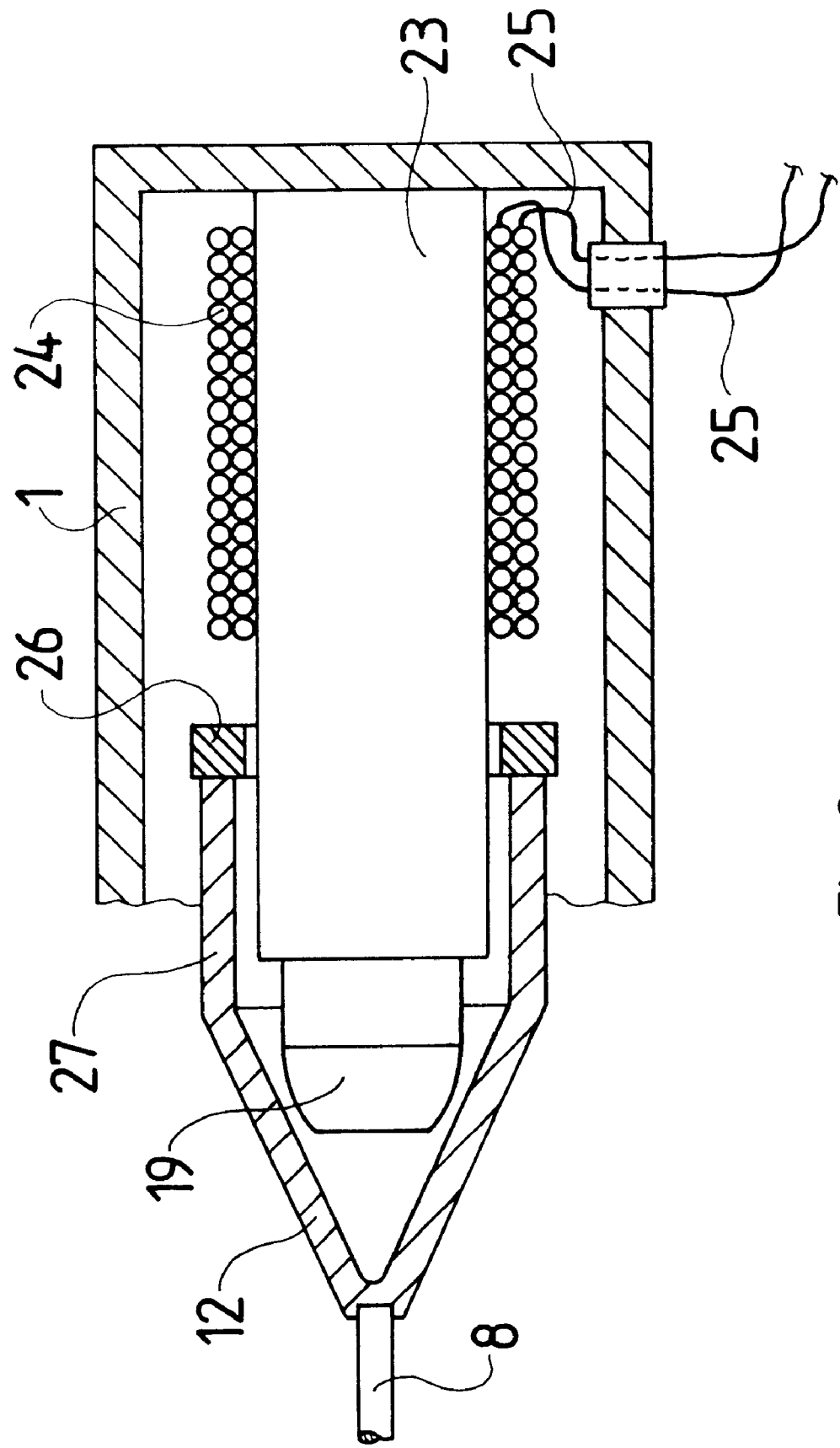
FIG. 2 is a detail of a view similar to FIG. 1 of a drive system of a second embodiment.

FIG. 2 shows another embodiment of the electrodynamic drive system of the impact wire. This Figure shows the right half of FIG. 1 as a modified embodiment while retaining as much as possible the references used in FIG. 1. The left-side portions of the apparatus omitted from FIG. 2 may wholly correspond to the embodiment of FIG. 1.

As shown by FIG. 2, a magnetizable core 23 made of a magnetically permeable material is affixed inside housing I at its proximal end and coaxially with the axial direction of impact wire 8 and carries at its proximal end a winding 24 connected by electrical leads 25 to external electrical pulse generator 15 (omitted from FIG. 2). A shorting coil in the form of a closed ring 26 is mounted coaxially with core 23 and is freely axially displaceable, and furthermore it is coupled by a cylindrical extension 27 of funnel 12, for instance by bonding or any other play-free connection, to this funnel which is connected to impact wire 8 as in the embodiment of FIG. 1.

When a current pulse is applied to winding 24, it induces in the manner of a transformer, by means of magnetizable core 23, a short current in ring 26, of opposite direction to that of the current in winding 24. As a result, ring 26, which also may comprise several separate shorted turns, and together with it through the intermediary of the coupling element, impact wire 8, is accelerated with great force in the axial direction away from winding 24.

The underlying physics is known as the "Elihu Thompson experiment" and is described in the textbook "Physik" by Christian Gerthsen, Springer, 1963, p 265, FIG. 341.

On account of the short current induced in it, ring 26 is accelerated in the magnetic field generated impulsively by electromagnets 23, 24. The design shown in FIG. 2 can be improved further if the field lines generated by the electromagnets 23, 24 are concentrated radially to the axis in the region of ring 26. This feature can be attained by imparting a geometry of core 23 similar to that of a permanent magnet 2 of the embodiment of FIG. 1, namely comprising an external pole piece 4 generating a strong radial magnetic flux between its end and that of the inner pole piece at the site of ring 26.

The embodiment of FIG. 2 also allows some play in transmission. In particular, ring 26 is mounted in separate manner from the funnel 12, as a result of which it impacts this funnel after having moved along a short path.

Figure 3:
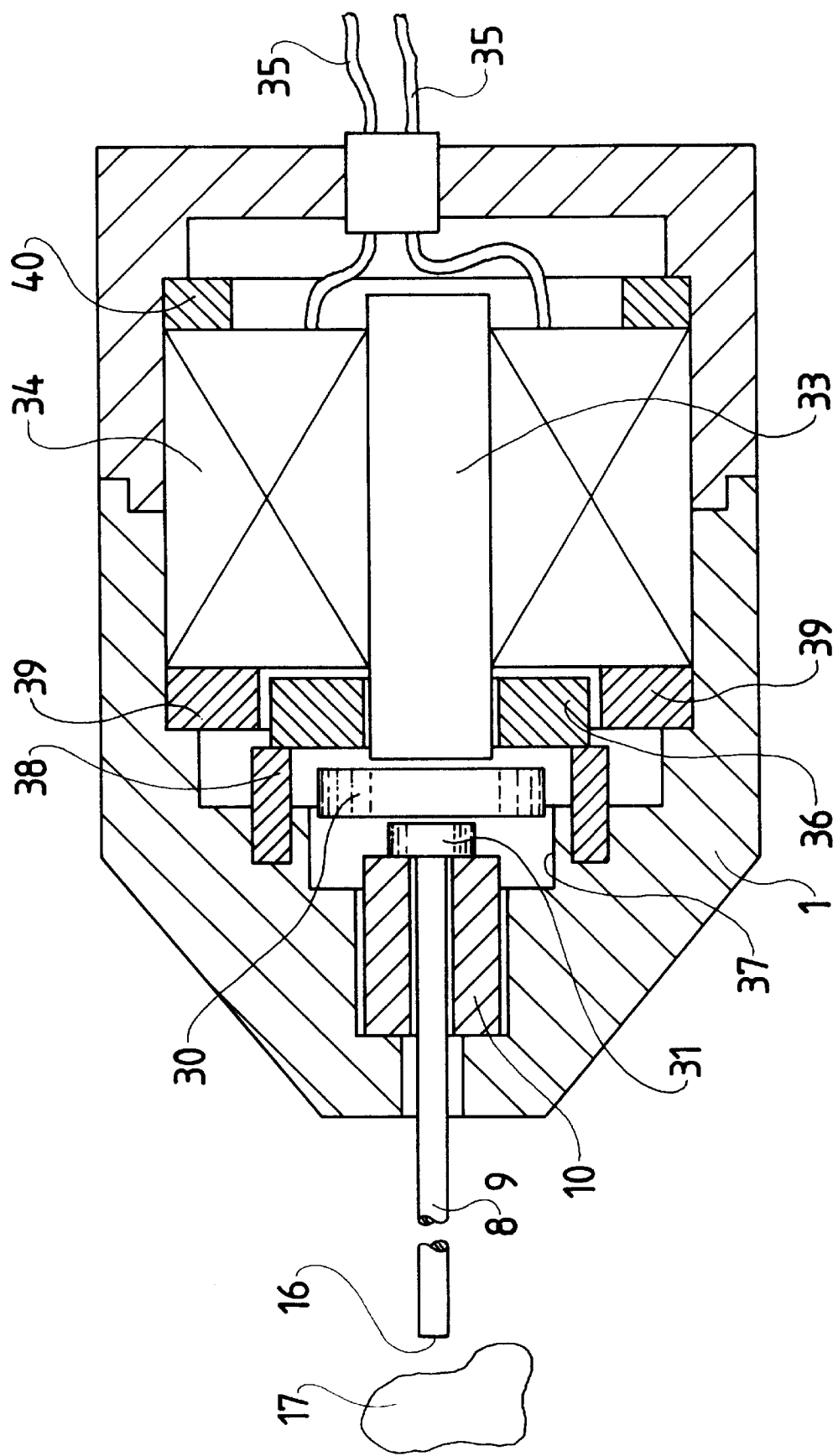
FIG. 3 is an axial section of a third embodiment of an apparatus in accordance with the invention.

FIG. 3 shows a third preferred embodiment of the invention which is especially characterized by high design simplicity and which basically corresponds to the embodiment of FIG. 2. Again the reference numerals of FIGS. 1 and 2 are used here as much as possible.

Housing 1 is separable and may consist merely of plastic or also of a material with magnetic and/or electrical shielding properties, and it receives impact wire 8 and elastic block 10 in the same manner as described in the above embodiments. In the embodiment of FIG. 3, however, this impact wire comprises an enlarged head 31 at its proximal end where it will be impacted and which also implements the rest against elastic block 10. In this embodiment also block 10 may seal the impact wire 8 in a liquid-tight manner relative to the housing.

A magnetizable core 33 made of an appropriately magnetically permeable material is configured coaxially with impact wire 8, being affixed in a winding 34 which in turn is affixed in housing 1 in the manner shown. Winding 34 is connected by electrical leads 35 to pulse generator 15 as in FIG. 1.

A ring 36, illustratively made of aluminum, rests on the free end of core 33 projecting winding 34 toward impact wire 8 and is freely axially displaceable on this core 33. A plate 30 is mounted transversely to the axial direction of core 33 between head 31 of impact wire 8 and the facing end of core 33 and acts as a coupling system replacing funnel 12 shown in FIGS. 1 and 2. Plate 30 is radially guided at its periphery inside a suitable clearance 37 of housing 1 while permitting axial displacement.

Housing 1 furthermore receives an elastic ring 38 which weakly presses ring 36, acting as a coil, toward winding 34 to come to rest against it in its rest position.

Accordingly, in its rest position, due to the spring loading by elastic ring 38, aluminum ring 36 rests against the end face of winding 34. By means of elastic block 10, head 31 of impact wire 8 is pushed against the central zone of plate 30 which in the rest position is thereby forced against the end face of core 33.

If now winding 34 is energized by a current pulse, then an axial magnetic flux is generated in core 33. This flux induces an opposing current in ring 36, as a result of which this ring is accelerated in the magnetic field of core 33 toward impact wire 8. Ring 36 then rests annularly on the outer zones of plate 30 which in turn impacts impact wire 8 through its head 31. When using pulse generator 15 described in relation to FIG. 1, the embodiment of FIG. 3 allows exceedingly hard impact pulses in impact wire 8 allowing efficient destruction of stone 17.

For clarity, head 31, plate 30, core 33 and ring 36 are shown mutually apart in FIG. 3. In the actual embodiment, even when plate 30 rests against core 33 (due to the force from elastic block 10), and in the reset position wherein the ring 36 rests against the winding 34, there will be a slight gap between plate 30 and the ring 36. Upon applying an impact current to the winding 34, ring 36 therefore is first accelerated in unhampered manner over a short distance before impacting plate 30. This feature offers a somewhat longer stroke of ring 36 and hence improved utilization of the energy of the generated magnetic field.

However, ring 36 may rest against plate 30 when in the rest position. No more is required in the embodiment of FIG. 3 than to slightly shorten core 33. In that case, head 31, plate 30 and ring 36 may be firmly coupled to each other, for instance by bonding. This too allows enormously hard impact waves in impact wire 8.

As shown in FIG. 3, a field ring 39 enclosing ring 36 can be affixed to the end face of winding 34 facing impact wire 8. This field ring is made of a magnetizable, that is a magnetically permeable material, care being required that no circulating currents are induced in it. Illustratively a slotted iron material or a ferrite may be used. Field ring 39 shapes the magnetic field generated by electromagnets 33, 34 in the zone of ring 36 in such a way that ring 36 is crossed by a high magnetic field radially to the axis. A suitably formed further field ring 40 of the rear end face of winding 34 may additionally shape the magnetic field in advantageous manner.

As regards the embodiment shown in FIG. 3, head 31, plate 30, ring 36, core 33 and coil 34 may assume circular cross-sections. However, rectangular or other cross-sections are also admissible. Plate 30 is made of an optimally lightweight, bending-resistant material. By resort to a suitable, for instance laminar design, care must be taken to avoid eddy currents in core 33.

In the above described embodiments of the apparatus of the invention, impact wire 8 is used as a transmitter introducing the impact pulse into the human body. The application therefore relates to destroying concretions, for instance gall stones, but in particular stones in the field of urology, for instance in the renal duct.

However, when slightly modified, the apparatus of the invention also may be used to introduce impact pulses into the human body through a tissue surface, for instant the dermal surface. In that case the transmitter, instead of being an impact wire 8, for instance may be in the form of the plate 30 of FIG. 3.

It is seen by examining FIG. 3 that by omitting impact wire 8 and block 10, plate 30, upon appropriate modification of the housing 1, can be directly mounted in a housing opening against the edge of which this plate is illustratively kept by means of an elastic membrane in sealing manner. The apparatus of this embodiment then can be deposited by means of plate 30 on a tissue surface, for instance the dermal surface, to introduce impact pules across a surface into the tissue.

Again, variations are feasible with respect to the embodiments of FIGS. 1 and 2 wherein impact wire 8 is replaced by a transmitter of comparatively large area to introduce impacts into body surfaces.

What is claimed is:

1. An apparatus to introduce impact pulses into the human body comprising
   an impact transmitter (8) displaceable in an axial direction;
   a source of current pulses;
   an electromagnetic impact generator (2, 6; 26, 24; 36, 34) driven by current pulses from said source and supplying impact impulses to said impact transmitter, said impact generator comprising
      a magnet fixed in position and capable of producing a magnetic field, and
      a coil (6, 26, 36) displaceable in said direction of transmitter displacement in said field of said magnet (2; 23, 24; 33, 34), said coil being energized by said current pulses to be axially displaced and drive said transmitter (8).

2. An apparatus according to claim 1 wherein said current pulses are directly applied to said coil (6) through flexible electrical connecting leads (13), said coil being mounted with its current guide direction perpendicular to said direction of displacement of said impact transmitter (8) and perpendicular to field lines of said magnet (2).

3. An apparatus according to claim 1 wherein said impact transmitter (8) has a proximal end face, said apparatus comprising a coupling structure (12, 30) for delivering impact force to said impact transmitter from said coil (6, 26, 36) through said coupling structure (12, 30).

4. An apparatus according to claim 3 wherein said coupling structure has a shape of a funnel (12).

5. An apparatus according to claim 3 wherein said coupling structure has the shape of a plate (30) in a plane perpendicular to said direction of displacement of said impact transmitter (8), said plate being positioned to contact at its edges said coil (36) and at its middle on an opposite side with said impact transmitter (8).

6. An apparatus according to claim 1 wherein said coil is an inductively loaded shorted turn (26, 36) mounted coaxially with a stationary winding (24, 34) of an electromagnet (23,24; 33,34).

7. An apparatus according to claim 6 wherein said electromagnet comprises a core (23, 33) stationary in said displacement direction of said impact transmitter (8) and comprises a magnetically permeable material, said winding (24, 34) being affixed to said core and said shorted turn (26, 36) being displaceable on said core in the direction of impact transmitter displacement.

8. An apparatus according to claim 7 comprising a field ring (39) comprising a magnetically permeable material affixed to an end face of said winding (34) facing said shorted turn (36) and radially enclosing said shorted turn.

9. An apparatus according to claim 1 wherein said impact transmitter is an impact wire (8) insertable into a body of a patient to contact a concretion (17) with a distal end face of said transmitter and to mechanically destroy said body concretion (17).

* * * * *